US009883939B2

(12) United States Patent
Yamada et al.

(10) Patent No.: US 9,883,939 B2
(45) Date of Patent: Feb. 6, 2018

(54) REDUCING IMMUNOGENICITY OF XENOGENEIC TRANSPLANT TISSUES

(71) Applicant: The General Hospital Corporation, Boston, MA (US)

(72) Inventors: Kazuhiko Yamada, Chestnut Hill, MA (US); J. Scott Arn, North Andover, MS (US); Curtis L. Cetrulo, Cohasset, MA (US); David H. Sachs, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/399,119

(22) PCT Filed: May 8, 2013

(86) PCT No.: PCT/US2013/040179
§ 371 (c)(1),
(2) Date: Nov. 5, 2014

(87) PCT Pub. No.: WO2013/169929
PCT Pub. Date: Nov. 14, 2013

(65) Prior Publication Data
US 2015/0164634 A1 Jun. 18, 2015

Related U.S. Application Data

(60) Provisional application No. 61/783,243, filed on Mar. 14, 2013, provisional application No. 61/644,163, filed on May 8, 2012.

(51) Int. Cl.
| | |
|---|---|
| A61F 2/10 | (2006.01) |
| A61L 27/36 | (2006.01) |
| A61L 27/60 | (2006.01) |
| C12Q 1/70 | (2006.01) |
| A61K 35/12 | (2015.01) |
| A01K 67/027 | (2006.01) |
| A61K 35/36 | (2015.01) |

(52) U.S. Cl.
CPC .......... *A61F 2/105* (2013.01); *A01K 67/0271* (2013.01); *A61K 35/12* (2013.01); *A61K 35/36* (2013.01); *A61L 27/3604* (2013.01); *A61L 27/60* (2013.01); *C12Q 1/705* (2013.01); *A01K 2227/108* (2013.01); *A01K 2267/02* (2013.01); *C12N 2710/16111* (2013.01)

(58) Field of Classification Search
None
See application file for complete search history.

(56) References Cited

U.S. PATENT DOCUMENTS

| | | | |
|---|---|---|---|
| 5,614,187 A | 3/1997 | Sachs | |
| 5,843,425 A | 12/1998 | Sachs et al. | |
| 5,849,991 A | 12/1998 | D'Apice et al. | |
| 6,153,428 A | 11/2000 | Gustafsson et al. | |
| 6,306,651 B1 | 10/2001 | Sachs | |
| 6,413,769 B1 | 7/2002 | Gustafsson et al. | |
| 6,469,229 B1 * | 10/2002 | Sachs ................... | A01K 67/027 800/17 |
| 6,558,663 B1 * | 5/2003 | Seebach ............... | A61K 39/001 424/93.2 |
| 6,849,448 B1 | 2/2005 | D'Apice et al. | |
| 7,037,900 B2 * | 5/2006 | DiMartino .......... | A61K 31/7056 514/42 |
| 7,141,716 B2 | 11/2006 | Sachs et al. | |
| 7,201,899 B2 | 4/2007 | D'Apice et al. | |
| 2003/0014770 A1 * | 1/2003 | Gustafsson ........ | A01K 67/0275 800/17 |
| 2006/0147428 A1 | 7/2006 | Sachs | |
| 2007/0033668 A1 | 2/2007 | Sachs et al. | |
| 2013/0111614 A1 | 5/2013 | McGregor et al. | |

FOREIGN PATENT DOCUMENTS

| | | |
|---|---|---|
| AU | 695373 | 8/1995 |
| AU | 711144 | 1/1998 |
| EP | 0755451 | 5/2005 |
| WO | 1995020661 | 8/1995 |
| WO | 2004/028243 | 8/2004 |

OTHER PUBLICATIONS

Mueller et al. (Transplantation. 2004; 78 (10): 1449-1453).*
Weiner et al. (Xenotransplantation. 2010; 17: 147-152).*
Sachs et al. (Genetically Modified Porcine Skin Grafts for Treatment of Severe Burn Injuries). Massachusetts General Hospital Boston, 2010.*
Whitteker et al. (Transplantation. 2008; 86 (1): 155-162).*
Swindle. (Annals of the New York Academy of Sciences. 1998; 862 (1): 111-120).*
Steve et al. (Annals of Surgery: Oct. 208; 248 (4): 564-577, abstract only).*
Rike et al. (Clinical Transplantation: Mar./ Apr. 2008; 22 (2): 229-235, abstract only).*
Hwang et al. (Diseases of the Colon and Rectum: Dec. 10; 53 (12): 1699-1707, abstract only).*
International Preliminary Report on Patentability in International Application No. PCT/US2013/040179, dated Nov. 11, 2014, 6 pages.
Ben-Bassat, "Performance and safety of skin allografts," Clin Dermatol., Jul.-Aug. 2005;23(4):365-75.
Desai et al., "Early burn wound excision significantly reduces blood loss," Ann Surg., Jun. 1990;211(6):753-9.
Fishman and Rubin, "Infection in organ-transplant recipients," N Engl J Med., Jun. 11, 1998;338(24):1741-51.
Food and Drug Administration, Center for Biologics Evaluation and Research, Guidance for Industry: Source Animal, Product, Preclinical, and Clinical Issues Concerning the use of Xenotransplantation in Humans. FDA/CBER/DCGT /LCI (HFM-40), 1401 Rockville Pike, Rockville, MD 20852, USA. Available online at fda.gov/cber/guidelines.htm)., 63 pages, 2003.

(Continued)

*Primary Examiner* — Shanon A. Foley
(74) *Attorney, Agent, or Firm* — Leason Ellis LLP (57) ABSTRACT

Methods of preparing and porcine cells, organs and tissues that have reduced immunogenicity, e.g., for transplant into humans, e.g., for the treatment of burn injuries.

11 Claims, 2 Drawing Sheets

(56) References Cited

OTHER PUBLICATIONS

Galili et al., "Man, apes, and Old World monkeys differ from other mammals in the expression of alpha-galactosyl epitopes on nucleated cells," J Biol Chem., Nov. 25, 1998;263(33):17755-62.
Griesemer et al., "Results of gal-knockout porcine thymokidney xenografts," Am J Transplant., Dec. 2009;9(12):2669-78.
Guedes et al., "Reactivation of porcine cytomegalovirus through allogeneic stimulation," J Clin Microbiol., Apr. 2004;42(4):1756-8.
Hamel et al., "PCR assay for detecting porcine cytomegalovirus," J Clin Microbiol., Nov. 1997;37(11):3767-8.
Harunari et al., "Histology of the thick scar on the female, red Duroc pig: final similarities to human hypertrophic scar," Burns, Sep. 2006;32(6):669-77.
Hermans, "Preservation methods of allografts and their (lack of) influence on clinical results in partial thickness burns," Burns., Aug. 2011;37(5):873-81.
Hettiaratchy and Dziewulski, "ABC of burns: pathophysiology and types of burns," BMJ, Jun. 12, 2004;328(7453):1427-9.
Kearney, "Guidelines on processing and clinical use of skin allografts," Clin Dermatol., Jul.-Aug. 2005;23(4):357-64.
Klymiuk et al., "Genetic modification of pigs as organ donors for xenotransplantation," Mol Reprod Dev., Mar. 2010;77(3):209-21.
Kolber-Simonds et al., "Production of alpha-1,3-galactosyltransferase null pigs by means of nuclear transfer with fibroblasts bearing loss of heterozygosity mutations," Proc Natl Acad Sci USA, May 11, 2004;101(19):7335-40.
Lari and Gang, "Expansion technique for skin grafts (Meek technique) in the treatment of severely burned patients," Burns, Feb. 2001;27(1):61-6.
Mezrich et al., "Histocompatible miniature swine: an inbred large-animal model," Transplantation, Mar. 27, 2003;75(6):904-7.
Orgill, "Excision and skin grafting of thermal burns," N Engl J Med., Feb. 26, 2009;360(9):893-901.
Ozato et al., "Monoclonal antibodies to mouse major histocompatibility complex antigens," Transplantation, Sep. 1982;34(3):113-20.
Sachs et al., "The immunologic response to xenografts. Recognition of mouse H-2 histocompatibility antigens by the rat," J Immunol., Aug. 16971;107(2):481-92.
Schechter, "Prolonged retention of glutaraldehyde-treated skin allografts and xenografts: immunological and histological studies," Ann Surg., Dec. 1975;182(6):699-704.
Shimizu and Yamada, "Histopathology of xenografts in pig to non-human primate discordant xenotransplantation," Clin Transplant., Jul. 2010;24 Suppl 22:11-5.
Simon et al., "The pig as an experimental animal model of percutaneous permeation in man: qualitative and quantitative observations—an overview," Skin Pharmacol Appl Skin Physiol., Sep.-Oct. 2000;13(5):229-34.
Sullivan et al., "The pig as a model for human wound healing," Wound Repair Regen., Mar.-Apr. 2001;9(2):66-76.
Vandeput et al., "A review of skin meshers," Burns, Aug. 1995;21(5):364-70.
Vodicka et al., "The miniature pig as an animal model in biomedical research," Ann N Y Acad Sci, May 2005;1049:161-71.
Wainwright et al., "Clinical evaluation of an acellular allograft dermal matrix in full-thickness burns," J Burn Care Rehabil., Mar.-Apr. 1996;17(2):124-36.
Wang et al., "The application of new biosynthetic artificial skin for long-term temporary wound coverage," Burns, Dec. 2005;31(8):991-7.
Wang et al., "Survival and wound contraction of full-thickness skin grafts are associated with the degree of tissue edema of the graft bed in immediate excision and early wound excision and grafting in a rabbit model," J Burn Care Res., Jan.-Feb. 2007;28(1):182-6.
Weiner et al., "Prolonged survival of GalT-KO swine skin on baboons," Xenotransplantation, Mar.-Apr. 2010;17(2): 147-52.
Yamada et al., "Role of the thymus in transplantation tolerance in miniature swine. I. Requirement of the thymus for rapid and stable induction of tolerance to class I-mismatched renal allografts," J Exp Med., Aug. 18, 1997;186(4):497-506.
Yamada et al., "Marked prolongation of porcine renal xenograft survival in baboons through the use of alpha1,3-galactosyltransferase gene-knockout donors and the cotransplantation of vascularized thymic tissue," Nat Med., Jan. 2005;11(1):32-4.
Yang and Sykes, "Xenotransplantation: current status and a perspective on the future," Nat Rev Immunol., Jul. 2007;7(7):519-31.
Zhong et al., "Improvement in human decay accelerating factor transgenic porcine kidney xenograft rejection with intravenous administration of gas914, a polymeric form of alphaGAL," Transplantation, Jan. 15, 2003;75(1):10-9.
Zhu et al., "Further similarities between cutaneous scarring in the female, red Duroc pig and human hypertrophic scarring," Burns, Sep. 2004;30(6):518-30.
PHS Guideline on Infectious Disease Issues in Xenotransplantation, 2001, pp. 1-59. Retrieved from the Internet URL: http://www.fda.gov/biologicsbloodvaccines/guidancecomplianceregulatoryinformation/guidances/xenotransplantation/ucm07 4 72 7.html.
Nicolas J. Mueller et al. Activation of Cytomegalovirus in Pig-to-Primate Organ Xenotransplantation, Journal of Virology, 2002, vol. 76, No. 10, pp. 4734-4740.
D.S. Chatterjee. A controlled comparative study of the use of porcine xenograft in the treatment of partial thickness skin loss in an occupational health centre. Current Medical Research and Opinion, 1978, vol. 5, No. 9, p. 726-733.
Robert E. Michler. Xenotransplantation: Risks, Clinical Potential, and Future Prospects. Emerging Infectious Diseases, 1996, vol. 2, No. 1, p. 64-70.
Cloned Knockout Mini-pigs Hold Potential for Organ Xenotransplantation. Reuter's Health, 2004, Retrieved from the Internet <URL: https://www.perfusion.com/cgibin/absolutenm/anmviewer.asp?articleid=1615&zoneid=8, p. I.
H. Niemann et al. Progress in Xenotransplantation Research Employing Transgenic Pigs. Transplantationsmedizin, 2003, 15,pp. 3-14.
International Search Report and Written Opinion dated Sep. 5, 2013 in international application No. PCT/US2013/040179, 8 pgs.

\* cited by examiner

REDUCING IMMUNOGENICITY OF XENOGENEIC TRANSPLANT TISSUES

CLAIM OF PRIORITY

This application is a U.S. National Phase Application under 35 U.S.C. § 371 of International Patent Application No. PCT/US2013/040179, filed on May 8, 2013, which claims the benefit of U.S. Provisional Patent Application Ser. Nos. 61/644,163, filed on May 8, 2012, and 61/783,243, filed on Mar. 14, 2013. The entire contents of the foregoing are hereby incorporated by reference.

FEDERALLY SPONSORED RESEARCH OR DEVELOPMENT

This invention was made with Government support under Grant No. DR080729 awarded by the Department of Defense and Grant No. 5P01AI45897-09 awarded by the National Institutes of Health. The Government has certain rights in the invention.

TECHNICAL FIELD

This Application relates to methods of preparing and porcine cells, organs and tissues that have reduced immunogenicity, e.g., for transplant into humans, e.g., for the treatment of burn injuries.

BACKGROUND

Xenogeneic renal transplants from MGH Gal-knockout (GalT-KO) miniature swine to baboons performed prior to 2005 using chronic immunosuppressive regimens, survived longer (on average 29 days) than similar xenogeneic renal transplants from other sources of GalT-KO swine, performed at several other research centers (ca. 15 days) (Yamada et al., Nat Med 2005; 11:32-34; Zhong et al., Transplantation 2003; 75:10-19). Transplants at MGH using MGH GalT-KO donors and a tolerance-inducing regimen (i.e., thymokidney transplants) survived an average of 51 days (Yamada et al., 2005, supra; Griesemer et al., Am J Transplant 2009; 9:2669-2678). Though length of survival of the grafted materials is crucial, the reason for this much superior performance was not known.

SUMMARY

At least in part, the present invention is based on the discovery that using xenotransplant tissues obtained from a cytomegalovirus (CMV)-free porcine source results in extended transplant survival. Thus the methods described herein include determining that the tissues to be used for transplant, or the animal from which the tissues were derived, are CMV-free.

In a first aspect, the invention features methods for selecting a swine donor of a cell, tissue, or organ for use in a xenotransplant procedure. The methods include providing a sample comprising a cell or tissue from a candidate donor swine; performing an assay (e.g., a PCR or RT-PCR based assay) on the sample to detect the presence of latent or active porcine cytomegalovirus (pCMV) in the sample; identifying a candidate donor swine that is free of pCMV; and selecting the swine as a donor of a cell, tissue, or organ for use in a xenotransplant procedure.

In some embodiments, the sample comprises a cell or tissue from the cell, tissue, or organ that is to be used in the xenotransplant procedure.

In some embodiments, the methods include transplanting the cell, tissue, or organ into a recipient.

In some embodiments, the recipient is a human or non-human primate.

In another aspect, the invention provides methods for treating a subject, e.g., a human or non-human primate, who has suffered an injury requiring a skin graft. The methods include providing a sample comprising a cell or tissue from a candidate donor swine; performing an assay on the sample to detect the presence of latent or active porcine cytomegalovirus (pCMV) in the sample; identifying a candidate donor swine that is free of pCMV; and selecting the swine as a donor of a cell, tissue, or organ for use in a xenotransplant procedure; harvesting a skin graft from the donor swine, thereby providing a xenogeneic skin graft; and implanting the xenogeneic skin graft (i.e., a graft sized to cover the injured tissue) onto the injury in the subject.

In some embodiments, the methods include monitoring the xenogeneic skin graft for clinical signs of rejection; after detection of one or more clinical signs of rejection of the skin graft, removing the xenogeneic skin graft and replacing it with an allogeneic skin graft or an autologous skin graft.

In another aspect, the invention provides methods for treating a subject, e.g., a human or non-human primate, who has suffered an injury requiring a skin graft. The methods include implanting at the injured site a xenogeneic skin graft comprising skin from a donor swine (i.e., a graft sized to cover the injured tissue); monitoring the xenogeneic skin graft for clinical signs of rejection; after detection of one or more clinical signs of rejection of the xenogeneic skin graft, removing the xenogeneic skin graft and replacing it with an allograft; monitoring the allograft for one or more clinical signs of rejection; after detection of one or more clinical signs of rejection of the allograft, removing the allograft and replacing it with an autograft.

In some embodiments, the swine is a swine that expresses a transgene encoding a human MHC class I protein that inhibits recipient NK cell mediated attack; a swine which is homozygous at swine leukocyte antigens (SLA) A, B, C, DR, and DQ, and in which at least 60% of all other genetic loci are homozygous; and/or a swine in which the normal expression or function of alpha(1,3) galactosyltransferase is prevented in at least one organ of tissue type.

In some embodiments, the swine is a miniature swine.

In some embodiments, the one or more clinical signs of rejection are selected from the group consisting of lack or loss of vascularization, white or pale color compared to normal skin; cooler temperature as compared to normal skin; granulation; crust or scab formation; discharge; sloughing; and loss of or lessening of pliability.

In some embodiments, the xenogeneic skin graft is from a donor swine selected by a method including: providing a sample comprising a cell or tissue (e.g., skin or a skin cell, or a cell or tissue other than skin) from a candidate donor swine; performing an assay on the sample to detect the presence of latent or active porcine cytomegalovirus (pCMV) in the sample; identifying a candidate donor swine that is free of pCMV; and selecting the swine as a donor.

In some embodiments, the cell or tissue in the sample is renal, hepatic, vascular, splenic, or colonic, tissues; in lymph nodes, salivary glands, prostate, testes, or peripheral blood, e.g., macrophages, lymphocytes, or peripheral blood leukocytes.

In some embodiments of the methods described herein, the xenogeneic skin graft is cryopreserved after harvesting from the donor swine.

The skin grafting methods described herein can be used to treat any injury for which skin grafts are useful, e.g., for coverage of partial thickness and full thickness wounds including but not limited to burns, e.g. partial thickness or excised full thickness burn wounds; avulsed skin e.g. on an extremity; diabetic wounds, e.g., non-healing diabetic foot wounds, venous stasis ulcers.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

Top panel: Porcine CMV. The lanes were as follows:

| Lanes | Source | pCMV status |
|---|---|---|
| 1, 2, 3 and 4 | GalTKO kidneys from Meiji Unv. | Strongly positive |
| 5, 6, 7 | GalTKO kidneys from MGH/Nibs pigs. | Totally negative |
| 8 and 9 | CLAWN Gal + pigs | Weakly positive |

Bottom panel: endogenous gene: MHC-I; All positive.

FIG. 2 shows that baboon survival worsened since late 2008, to about 2 weeks or less survival time after transplant.

DETAILED DESCRIPTION

Optimizing survival time of xenotransplant cells, tissues, and organs is crucial to the success of these protocols; often, xenotransplant cells, tissues, and organs may be used as "temporary fixes" to keep a patient alive while an allogeneic or autologous transplant can be obtained. To avoid needing to do serial xenotransplants, and to provide the longest possible time to obtain the allogeneic or autologous cells, tissues, or organs, extended survival is desirable. Thus, the present methods of providing for longer-lived cells, tissues, or organs is critical to the success of these procedures.

Methods of Optimizing Transplant Success

The methods described herein include detecting latent or active CMV in tissues from a candidate donor swine, e.g., a transgenic swine, and selecting as a donor swine an animal that does not have latent or active CMV. The methods can further include transplanting the identified CMV-free cells, tissues, or organs into a recipient, e.g., a primate recipient, e.g., a human or non-human recipient.

Transgenic Swine for Use in Xenotransplant Protocols

A number of transgenic swine herds have been established that have reduced immunogenicity, and thus reduced likelihood of rejection, for use as cell, organ, or tissue donors in xenotransplantation protocols.

Antibodies that bind to alpha-1,3-galactosyltransferase (alpha-1,3-GalT encoded by GGTA1) initiate a rapid graft rejection process known as hyperacute rejection (Yang and Sykes, 2007); this can be avoided by using genetically modified donor pigs that lack functional GGTA1 expression (see, e.g., Yamada et al., Nat. Med. 2005; 11: 32-34; Ozato et al., Transplantation 1982; 34: 113-120; Mezrich et al., Transplantation 2003; 75: 904-907; Kolber-Simonds et al., Proc. Natl. Acad. Sci. U.S.A 2004; 101: 7335-7340). Alternatively or in addition, animals can be used that express human complement regulatory proteins such as CD46, CD55, CD59, or some combination thereof. Transgenes that confer human glycosylation can also be used, e.g., alpha-1, 2-fucosyltransferase (alpha-1,2-FT) or human beta-1,4-N-acetylglucosaminyltransferase III (GnT-III). Multi-transgenic pigs that harbor various combinations of these modifications can also be used. Transgenic strategies that can be used to overcome acute vascular rejection include the expression of human genes for CD39 (ecto-ADPase), endothelial protein C receptor (EPCR), heme oxygenase 1, thrombomodulin, and tissue factor pathway inhibitor (TFPI). Transgenes that overcome cell-mediated rejection can also be included. For a review, see Klymiuk et al., Molecular Reproduction & Development 77:209-221 (2010).

See, e.g., PG Pub No US2013/0111614 (transgenic pigs expressing reduced or no endogenous Sda or SDa-like glycans derived from the porcine beta1,4 N-acetyl-galactosaminyl transferase 2 (B4GALNT2) glycosyltransferase and/or reduced or no endogenous alpha-Gal antigens); US2003/0014770 (Transgenic swine in which the normal expression of alpha(1,3) galactosyltransferase is prevented in at least one organ of tissue type); 2007/0033668 (a swine which is homozygous for a major histocompatibility complex haplotype and at least 60% homozygous at all other genetic loci); U.S. Pat. No. 7,141,716 (Inbred miniature swine and uses thereof); U.S. Pat. No. 6,558,663 (Transgenic swine & swine cells having human HLA genes); U.S. Pat. No. 6,469,229 (Inbred miniature swine and uses thereof); U.S. Pat. No. 6,413,769 (alpha(1,3) galactosyltransferase negative porcine cells); U.S. Pat. No. 6,306,651 (Specific tolerance in transplantation); U.S. Pat. No. 6,153,428 (alpha(1,3) galactosyltransferase negative porcine cells); U.S. Pat. No. 6,030,833 (Transgenic swine and swine cells having human HLA genes); U.S. Pat. No. 5,843,425 (Transplantation and graft-versus-host-disease); U.S. Pat. No. 5,614,187 (Specific tolerance in transplantation).

Methods of Detecting Latent or Active CMV

The methods described herein can include a step of detecting the presence of latent or active CMV in a sample from a candidate donor animal. The sample can include a biological fluid such as blood, plasma, serum, or urine, or a fraction thereof; or can include cells or tissues. The cells or tissues can be obtained by biopsy, or can be obtained at time of harvest (i.e., when the cells, tissues, or organs are removed from the animal to be prepared for us in a transplant procedure, e.g., open sacrifice of the animal). In some embodiments, when cells or tissue are used, the cells or tissue to be tested are from the same organ that is to be used in a transplant procedure. In some embodiments, the cells or tissues to be tested are from a different organ or tissue than the cells, organ or tissue that are to be used in a transplant procedure. For example, the methods can include testing renal, hepatic, vascular, splenic, or colonic, tissues; in lymph nodes, salivary glands, prostate, testes, or peripheral blood, e.g., macrophages, lymphocytes, or peripheral blood leukocytes; in some embodiments, tissues other than or in addition to those tested are harvested for transplantation.

A number of methods known in the art can be used to detect latent or active CMV in the sample. For example, PCR- or RT-PCR-based methods can be used. In general, the methods will detect porcine CMV (pCMV). In some embodiments, a specific primer pair of the PCMV DNA polymerase gene can be used in the PCR and RT-PCRs: forward, 5-CCCTGATCTTAAATGACGAGGACGT-GAC-3 (SEQ ID NO:1); and reverse, 5-ACCGTCTGAGA-GACTGAACTTCTCTGACAC-3 (SEQ ID NO:2) (Hamel et al., J. Clin. Microbiol. 37:3767-3768 (1999); Guedes et al., J. Clin. Microbiol., 42(4):1756-1758 (2004)). See also Fishman and Rubin, N Engl J Med 338:1741-1751 (1998). In preferred embodiments, a method that is sensitive enough to detect latent CMV is used.

Transplantation of Xenogeneic Tissues, Cells, and/or Organs

A number of methods are known in the art for using the identified CMV-free tissues, cells and organs in transplant procedures. In some embodiments, the tissues, cells and organs are transplanted into a primate, e.g., a human or non-human primate. In some embodiments, the xenograft comprises skin, e.g., as described in Weiner et al., Xenotransplantation 2010; 17: 147-152). In some embodiments, transplant rejection is prevented or delayed by inducing tolerance in the subject, e.g., as described in Yamada et al., J. Exp. Med 1997; 186: 497-506, or US2006/0147428, using methods that include a step of introducing donor thymic tissue into the recipient. Alternatively or in addition, immunosuppressive therapies, e.g., administration of corticosteroids or radiation, can be used.

Serial Temporary Skin Grafting Methods

Approximately 500,000 burn injuries occur per year in the United States, of which 40,000 require admission to a burn center (Orgill, N Engl J Med 2009; 360: 893-901). In addition to the local injury inflicted, large burns, covering more than 30% total body surface, carry a significant risk of a severe systemic insult, with maintenance of temperature homeostasis following substantial skin loss requiring elevation of the metabolic rate up to three times above baseline. Additionally, activation of proinflammatory cytokine cascades can lead to a systemic inflammatory response, adult respiratory distress syndrome, and shock, while non-specific down regulation of the immune response, coupled with loss of the skin's natural barrier, renders the patient susceptible to opportunistic infections (Hettiaratchy and Dziewulski, BMJ 2004; 328: 1427-1429).

The current standard of care for burns requiring operative treatment is early burn excision and split thickness skin grafting (Wang et al., J Burn Care Res 2007; 28: 182-186; Desai et al., Ann Surg 1990; 211: 753-759). Autologous skin, harvested from non-burned regions of the patient's own body is preferred, however in large burns, sufficient donor sites may not be available to achieve the necessary coverage, even when meshed grafts are utilized (Lari and Gang, Burns 2001; 27: 61-66; Vandeput et al., Burns 1995; 21: 364-370). In cases where sufficient autologous skin is not available, allogeneic skin from deceased donors may be grafted to provide temporary coverage. While this allows for rapid coverage of the burn wound, allogeneic skin is eventually rejected and therefore does not provide definitive closure. Issues such as cost, limited availability and the potential for transmission of pathogens must also be considered when deceased-donor allografts are used. A number of alternative synthetic and biological dressings have been developed, but all share a susceptibility to infection, and high cost (Wainwright et al., J Burn Care Rehabil 1996; 17: 124-136; Wang et al., Burns 2005; 31: 991-997).

Porcine skin is recognized to share many of the characteristics of human skin (Harunari et al., Burns 2006; 32: 669-677; Simon et al., Skin Pharmacol Appl Skin Physiol 2000; 13: 229-234; Sullivan et al., Wound Repair Regen 2001; 9: 66-76; Vodicka et al., Ann N Y Acad Sci 2005; 1049: 161-171; Zhu et al., Burns 2004; 30: 518-530). Glutaraldehyde-fixed porcine skin has been used for temporary coverage of third degree burns (Schechter, Ann Surg 1975; 182: 699-704), however fixed skin compares poorly to vital skin, as it fails to vascularize and functions only as a biological dressing. Vital porcine skin cannot readily be used in this role due to its susceptibility to rapid rejection mediated by naturally circulating, pre-formed antibodies (Shimizu and Yamada, Clin Transplant 2010; 24 Suppl 22: 11-15). The major cell surface target for these antibodies is the alpha-galactosyl epitope which is present in all mammals except for Old World primates and humans (Galili et al., J Biol Chem 1988; 263: 17755-17762).

Genetically modified alpha-1,3 galactosyltransferase knockout inbred (GalT-KO) miniature swine, which lack the alpha-galactosyl epitope, have been described, and prolonged survival of skin from these animals transplanted across a pig-to-baboon barrier has been reported (Weiner et al., Xenotransplantation 2010; 17: 147-152). In those studies, skin grafts from these GalT-KO swine had comparable survival to allogeneic skin in baboons and thus might provide a new source of vital skin grafts for the acute treatment of severe burns.

In the present methods, the donor animals can be selected using a method described herein to identify animals that are pCMV-free, to optimize the survival time and reduce the chance of rejection of the graft. In some embodiments, the skin can be preserved, e.g., cryopreserved using known methods, see, e.g., Hermans, Burns. 2011 August; 37(5): 873-81; Kearney, Clin Dermatol. 2005 July-August; 23(4): 357-64; and Ben-Bassat, Clin Dermatol. 2005 July-August; 23(4):365-75, before use.

EXAMPLES

The invention is further described in the following examples, which do not limit the scope of the invention described in the claims.

Example 1. Reduced Immunogenicity of Porcine-Origin Xenografts

As noted above, xenogeneic renal transplants from MGH Gal-knockout (GalT-KO) miniature swine to baboons performed prior to 2005 had greatly superior survival than similar xenogeneic renal transplants from other sources of GalT-KO swine, performed at several other research centers (Zhong et al., Transplantation 2003; 75:10-19). Transplants at MGH using MGH GalT-KO donors and a tolerance-inducing regimen (i.e. thymokidney transplants) survived an average of 51 days (Table 1, part A) (Yamada et al., 2005, supra; Griesemer et al., Am J Transplant 2009; 9:2669-2678). The reason for this much superior performance was not known. After 2007, xenogeneic renal transplants at MGH using MGH GalT-KO donors survived only an average of 14.5 days, regardless of treatment regimen (Table 1, part B; Table 2, part C; and FIG. 2). Testing of the kidney tissue from one rejected xenogeneic kidney demonstrated a high level of porcine CMV.

TABLE 1

Thymokidney: Induced-Tolerance Strategy

A. MGH Pigs Before 2005 - Thymokidney Tx*
Average 50.9 days (n = 7)
Exclude Baboon CMV and Drug reaction = 61.8 days (n = 5)

| | |
|---|---|
| B134 | 83 days |
| B171 | 28 days (Baboon CMV+) |
| B178 | 40 days |
| B182 | 57 days (pCMV− tested) |
| B187 | 81 days |
| B189 | 18 days (DRUG reaction) |
| B194 | 49 days (CMV− tested). |
| | (B194 is the last animal in this series that was pCMV−) |

B. MGH Pigs Porcine CMV+ (tested) thymokidney Tx
Average 14.5 days

| | |
|---|---|
| B246 | 15 days (Kidney = Strong pCMV+) |
| B245 | 16 days (Kidney = Strong pCMV+) |
| B244 | 14 days (Kidney = Strong pCMV+) |
| B254 | 11 days (Kidney = Strong pCMV+) |
| B278 | 14 days (Kidney = Strong pCMV+; Baboon LN pCMV+) |
| B340 | 19 days (Kidney = Strong pCMV+) |
| B336 | 13 days (Kidney = Strong pCMV+) |

C. MGH Pigs delivered by C section - Either Thymokidney or Intra BM + Kid Average 53.0 days (n = 3)

| | |
|---|---|
| B336 | 60 days after kidney Tx (intra bone Bx prior to KTx) |
| B344 | 47 days after kidney Tx (intra bone Bx prior to KTx) |
| B341 | 52 days (Thymokidney) |

*Griesemer et al., Am J Transplant 2009; 9: 2669-2678.

TABLE 2

Kidney: Chronic Immunosuppression Strategy

A. MGH Pigs in TBRC Before 2005
Kidney Tx alone**
Average 29 days (n = 3) (likely pCMV−)

| | |
|---|---|
| B126 | 34 days (rejection) |
| B114 | 33 days (rejection) |
| B131 | 20 days (rejection) |

B. MGH/Nibs clone pigs in Kagoshima, Japan in 2010-12.
Kidney Tx alone
Average 28.7 days (n = 3)
MGH cells from 2007 and pCMV−

| | |
|---|---|
| B23408 | 29 days (rejection) |
| B23411 | 30 days (stable cre but severe nephrose/proteinuria) |
| B23413 | 27 days (rejection) |

C. Meiji Pigs in Kagoshima, Japan in 2010-12.
Kidney Tx alone
Average 12.8 days (n = 4)
All died due to rejection or LOW PLT/DIC
ALL pCMV+

| | |
|---|---|
| B22406 | 8 days (rejection) |
| B22405 | 14 days (rejection) |
| B22404 | 6 days (Low PLT DIC) |
| B23409 | 23 day (rejection) |

**Yamada et al., Nat Med 2005; 11: 32-34

Subsequent to this finding, MGH GalT-KO donors were intentionally derived by Cesarean section in order to avoid potential contamination with viruses, including porcine CMV. Three xenogeneic kidney transplants using these Cesarean-derived GalT-K0 animals as donors have survived an average of 53 days (Table 1).

Figure 2:
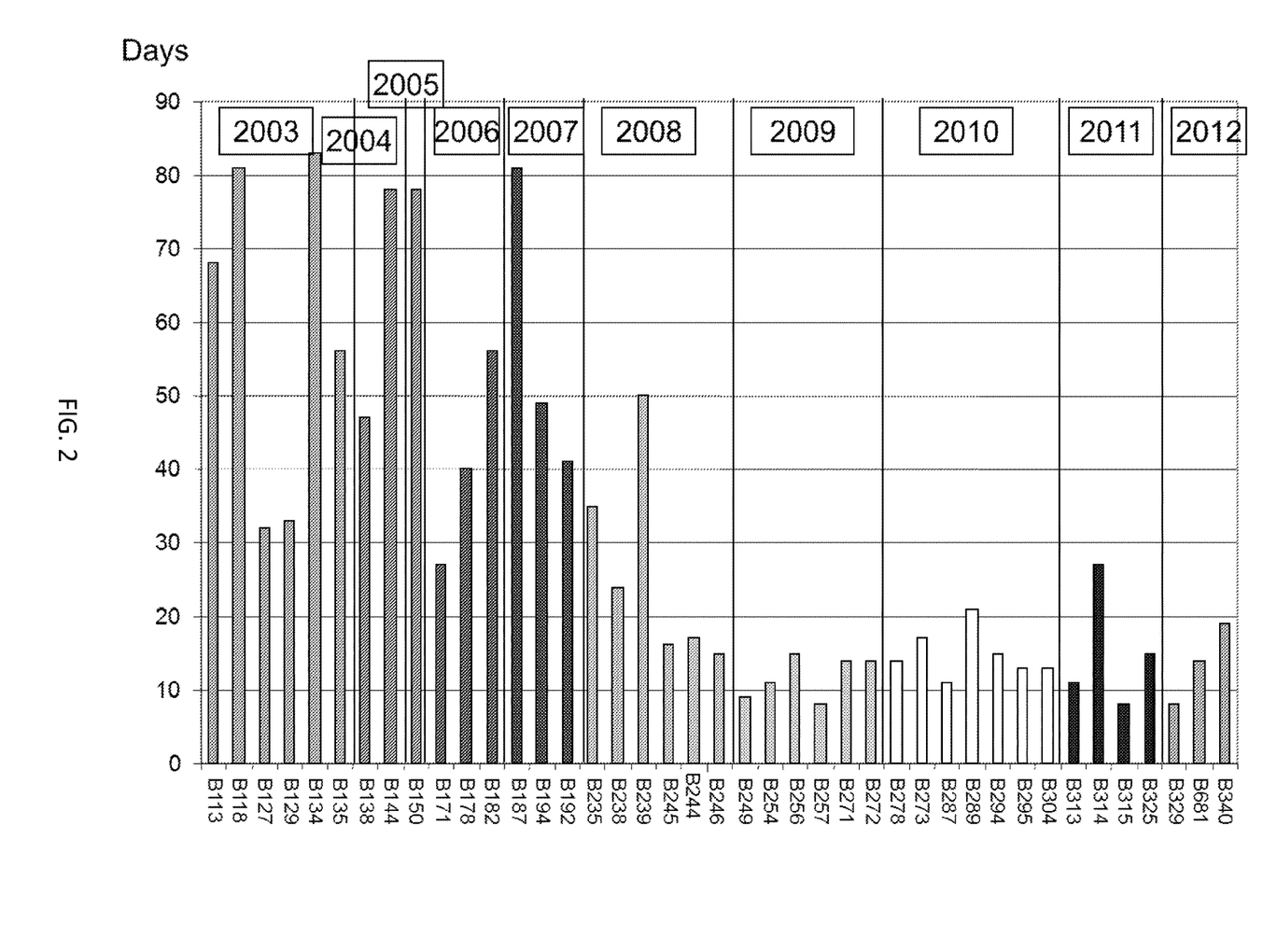
FIG. 2 is a bar graph showing graft survival of xeno thymokidney transplants between 2003 and 2012. Regimen: ATG followed by antiCD154 and MMF. Baboons who received BMTx and or had accidents like thrombosis were excluded from this analysis.

On the basis of these findings, it is believed that the reduced immunogenicity and superior survival of transplants from MGH GalT-KO animals, versus transplants from donors produced elsewhere, was due to the absence of a virus (as demonstrated herein, likely porcine CMV, which can be avoided by Cesarean derivation) in MGH GalT-KO animals that was present in other sources of GalT-KO animals. This virus was likely inadvertently introduced into the GalT-KO animals during the period between 2005 and 2007 (FIG. 2). The most recent data suggest that eliminating the virus by Cesarean derivation results in an increase in graft survival time.

Further confirmation of these findings has been provided by testing of xenogeneic renal transplants in a separate laboratory in Japan. In these studies, MGH GalT-KO swine were produced by nuclear transfer from fibroblasts obtained from animals prior to 2005 and stored frozen until shipped to Japan. Transplants were performed using either these MGH GalT-KO donors or donors from a Japanese colony of "Meiji GalT-KO" animals. The transplants from MGH GalT-KO animals survived an average of 28.7 days, while those from the Meiji animals survived an average of 12.8 days (Table 2, parts B and C).

Figure 1:
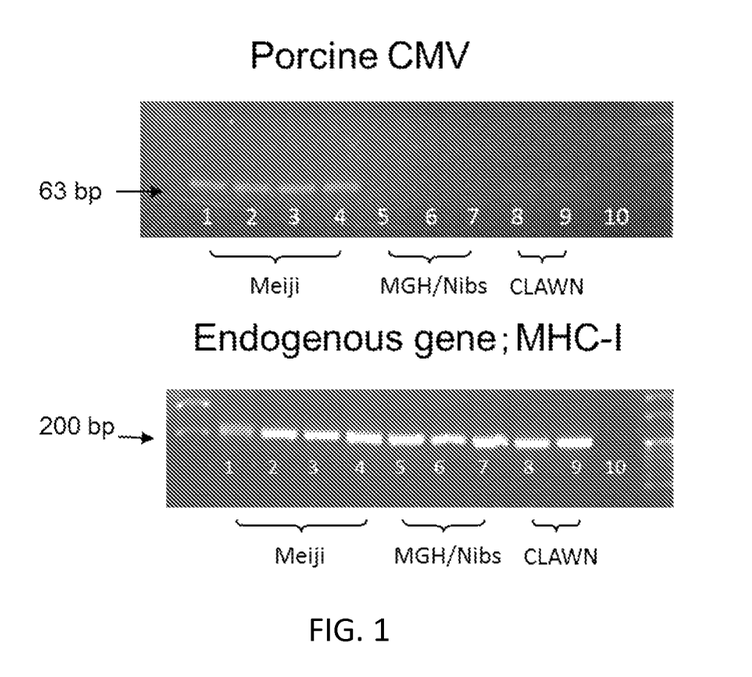
FIG. 1 is a pair of images showing the results of testing for pCMV and a control endogenous gene, MHC-1.

Studies of porcine CMV in tissue samples from the animals involved support the possibility that CMV may be the causative agent (FIG. 1).

Example 2. Lack of Cross-Sensitization Between Alpha-1,3-Galactosyltransferase Knockout Porcine and Allogeneic Skin Grafts Permits Serial Grafting In this current study the immune response against primary xenogeneic and allogeneic skin grafts was evaluated. In addition, the potential use of GalT-KO xenogeneic and allogeneic skin grafts in series was investigated in an attempt to provide an extended period of temporary wound coverage prior to definitive closure with autologous skin.

Materials and Methods

The following materials and methods were used in Example 2.

Animals

Baboons were obtained from an AAALAC approved breeding facility (Mannheimer Institute, Florida) and were between 1-2 years of age. Allogeneic donors were intentionally chosen to be MHC-mismatched, as indicated by pre-transplant mixed lymphocyte reactions. Xenogeneic donors were selected from the herd of MHC-defined GalT-KO MGH Miniature Swine.

Surgery

Under general anesthesia, 4×5 cm full thickness skin wounds were created on the dorsum of recipient baboons by excision of skin, subcutaneous tissue and fascia to reveal the underlying dorsal muscles. Hemostasis was achieved with electrocautery and a split thickness skin graft (allogeneic, xenogeneic or autologous) was placed. Grafts were sutured to the wound with interrupted 3-0 nylon sutures, which were removed between 7 and 12 days post operatively. Xenogeneic skin grafts were harvested from a GalT-KO swine donor under general anaesthesia, using an air-driven dermatome (Zimmer U.K. Ltd, Wiltshire, U.K.) set to 0.022 of an inch and were either cryopreserved or placed immediately on recipient. Frozen grafts were thawed no more than 6 hours prior to use. Allogeneic and autologous grafts were similarly harvested from baboons under general anaesthesia and placed directly on the recipient wound without cryopreservation. All grafts were dressed with a non-adherent pressure dressing, secured under a special primate jacket.

Isolation of Peripheral Blood Mononuclear Cells

Blood was drawn for pre-transplant and post-rejection mixed lymphocyte reactions (MLR), and analysis of serum antibodies. Peripheral blood mononuclear cells (PBMC) were isolated by gradient centrifugation in lymphocyte separation medium (Organon Teknika, Durham, N.C., USA) and re-suspended in AIM-V media (Invitrogen, Carlsbad, Calif., USA).

Serum Antibody Binding Assay

Swine and baboon PBMC were isolated from peripheral blood as described and counted by trypan blue exclusion. Cells where diluted to a concentration of $10 \times 10^6$ cells per mL in Flow Activated Cell Sorting media (1× Hanks Balanced Salt Solution with $Ca^+$ and $Mg^+$, 0.1% BSA and 0.1% sodium azide) and 100 µL added to each FACS tube. Serum samples were de-complemented in a 56° C. water bath for 30 min and serially diluted, starting at 1:10 and going out to 1:10,000, in FACS media. Volumes of 10 µL each of neat and diluted serum sample were added to the cells and incubated for 30 min at 4° C. Cells were washed twice before addition of 10 µL of a secondary antibody (FITC-conjugated goat anti-human or goat anti-swine IgM and IgG). Cells were incubated with the secondary antibody for 15 min at 4° C. and washed once with FACS media prior to acquisition on a FACScan (Becton Dickson, Franklin Lake, N.J.), using a Propidium Iodide gate. Flow cytometry data was analyzed using FlowJo (Tree Star Inc, Ashland, Oreg.).

Antibody-Mediated Complement-Dependent Cytotoxicity Assay

Antibody-mediated, complement-dependent cytotoxicity of serum from transplant recipients was measured using a modified version of the trypan blue dye exclusion lymphocytotoxicity technique of the National Institutes of Health (Patel et al., N Engl J Med 1969; 280: 735-739). Baboon sera, in two fold dilutions from 1:2 to 1:1024, were tested against baboon (skin donor) and GalT-KO porcine PBMC. Detection of permeabilized cells was performed using the florescent viability stain 7-actinoaminomycin D (7-AAD, Sigma). Samples were acquired using a FACScalibur (Becton Dickson, Franklin Lake, N.J.) and data analyzed in FlowJo. The cytotoxicity titer is defined as the dilution before the percentage cytotoxicity falls below 50% of maximum.

Results.

A. Xenogeneic Skin Grafts Survive in a Similar Manner to Allogeneic Skin Grafts

GalT-KO skin grafts were placed over full thickness defects on the dorsum of recipient baboons (n=4). Grafts rapidly adhered to the wound bed and showed signs of vascularization by postoperative day (POD) 4. All grafts remained viable, but with early signs of rejection, including darkening, crusting, and sloughing, at POD 10. Rejection was complete by POD12 or 13 in all cases. Following rejection of the GalT-KO grafts, subsequent grafts from allogeneic donors were placed on new wound beds. In similar fashion to the primary GalT-KO grafts, the allografts were rapidly adherent with signs of vascularization evident between POD 2 and 4, and the grafts remained intact and well-vascularized until POD 10, following which rejection progressed to completion between POD11 and 14. These results demonstrated that rejection of primary xenograft skin did not lead to accelerated rejection of a subsequent allograft.

A second group of baboons (n=4) received primary allogeneic skin grafts over full thickness defects. Similar to the primary GalT-KO grafts above, the primary allografts were adherent to the wound bed, demonstrated signs of vascularization between POD 2 and 4, and were viable at POD 10 but rejected between POD12 and 13. Following rejection of the primary allografts, these recipients then received xenogeneic GalT-KO grafts. Similar to the results observed for primary xenogeneic skin grafts, these secondary GalT-KO grafts underwent a time course of rejection that was comparable, with complete rejection by POD 10 to 13. These results demonstrated that rejection of subsequent GalT-KO xenografts was not accelerated following rejection of primary allografts. These results stand in contrast to the survival of second set grafts from the same donor as the first set Animals that received first set allografts had a survival of 11 days, while same donor second set allografts rejected in 4 days (n=2) Animals that received first set xenografts rejected in 11 days while the second set xenografts became white grafts, failing to vascularize and thus never becoming viable (n=2).

B. Rejection of Xenogeneic GalT-KO Skin does not Elicit a Cross-Sensitized Humoral Response to Subsequent Allografts:

While both T and B cell responses have been shown to play roles in the rejection of skin grafts, the lack of accelerated rejection of subsequent skin grafts in either the xeno/allo or allo/xeno series suggested that cross-sensitization was not occurring at a level sufficient to significantly affect the clinical outcome of the grafts. To assess the production of antibody to both xenogeneic and allogeneic antigens following skin grafts, binding of recipient serum IgM and IgG to PBMC targets from GalT-KO and allogeneic skin donors was measured by flow cytometry. Serum antibody levels were analyzed at multiple time points, including pre-grafting as well as post-rejection of first and second grafts. An increase in anti-xenogeneic IgM and IgG above pre-existing levels was detected (as shown by the increase in fluorescence of cells incubated with recipient serum) in all animals following rejection of primary GalT-KO xenogeneic skin grafts (summarized in Table 3 for IgG), and persisted for the duration of the study. These data correlated with the increase in anti-xenogeneic antibody-mediated cytotoxicity that was also observed following rejection of the GalT-KO skin graft.

Following subsequent allograft rejection, anti-allogeneic antibody binding to target PBMC could not be detected reliably by flow cytometry, with only one of four animals demonstrating an increase in anti-allogeneic antibodies in the IgG fraction. However, antibody-mediated anti-allogeneic cytotoxicity was demonstrated in all animals following rejection of these allografts, indicating that a response was mounted and had the capability to kill allogeneic cells. This anti-allogeneic antibody was not observed following rejection of the primary xenogeneic GalT-KO skin grafts until after rejection of the subsequent allogeneic grafts, further demonstrating that the rejection of the xenogeneic skin grafts did not lead to a cross-reactive anti-allogeneic response.

TABLE 3

| Baboon ID | Primary Graft (Donor) | Survival in Days | Anti-Xeno Ab FACS(†) | Anti-Allo Ab FACS(†) | Anti-Xeno Cytotox(■) | Anti-Allo Cytotox(■) |
|---|---|---|---|---|---|---|
| | | Post Primary Graft | | | | |
| B321 | Allo Fresh (B322) | 13 | 15 | 0 | 1:512 | 1:512 |
| B322 | Allo Fresh (B321) | 13 | 19 | 0 | 1:8 | 1:128 |
| B3411 | Allo Fresh (B3511) | 12 | 9 | 3 | 1:32 | >1:1024 |
| B3511 | Allo Fresh (B3411) | 13 | 0 | 65 | 1:32 | 1:64 |
| B297 | Xeno GalT-KO Fresh | 11 | *14 | 2 | 1:64 | N.D |
| B1011 | Xeno GalT-KO Fresh | 13 | 901 | 0 | 1:256 | 1:2 |
| B3811 | Xeno GalT-KO Freeze/Thawed | 12 | 447 | 1 | >1:1024 | 1:2 |
| B3911 | Xeno GalT-KO Freeze/Thawed | 13 | 729 | 1 | >1:1024 | 1:16 |
| | Secondary Graft (Donor) | Post Secondary Graft | | | | |
| B321 | Xeno GalT-KO Freeze/Thawed | 12 | 224 | 54 | >1:1024 | 1:512 |
| B322 | Xeno GalT-KO Freeze/Thawed | 13 | 1092 | 21 | 1:128 | 1:128 |
| B3411 | Xeno GalT-KO Freeze/Thawed | 12 | 1103 | 36 | >1:1024 | 1:1024 |
| B3511 | Xeno GalT-KO Freeze/Thawed | 10 | 1085 | 24 | >1:1024 | 1:512 |
| B297 | Allo Fresh (B293) | 10 | *51 | 0 | 1:16 | N.D |
| B1011 | Allo Fresh (B0911) | 11 | 1128 | 0 | 1:128 | 1:32 |
| B3811 | Allo Fresh (B3911) | 12 | 543 | 1 | 1:128 | 1:1024 |
| B3911 | Allo Fresh (B3811) | 14 | 1464 | 49 | >1:1024 | >1:1024 |

(†)Anti xenogeneic and allogeneic antibody binding data is shown as the delta mode of fluorescence intensity ($\Delta$MFI) of IgG antibody binding. The $\Delta$MFI is calculated by subtracting the MFI of the pre transplant time point from the MFI of the post rejection time points.
(■)The cytotoxicity titer is defined as the dilution after which percentage cytotoxicity falls below 50% of maximum.
N.D designates that the assay was not done.
*B297 had an abnormal antibody response, in comparison to other animals, producing IgM ($\Delta$MFI = 169) but low IgG ($\Delta$MFI = 14).

C. Rejection of Primary Allogeneic Skin does not Induce an Anti-Xenogeneic Humoral Response:

In the clinical setting, patients who may potentially require GalT-KO grafts for wound coverage may present with preformed anti-allogeneic antibodies due to previous exposures. As shown above, while we did not observe accelerated rejection of GalT-KO skin grafts following rejection of primary allogeneic grafts, we wished to further characterize whether recipients demonstrated any detectable production of anti-xenogeneic antibodies following rejection of the primary allogeneic graft. Anti-xenogeneic and anti-allogeneic IgM and IgG serum antibodies were assessed by both flow cytometry and cytotoxicity assays from baboons that received primary allografts and secondary xenografts. No increase in anti-xenogeneic antibodies above pre-existing levels was observed in either the IgM or IgG subclasses of antibody following rejection of the primary allogeneic skin grafts, but a significant increase in both following rejection of the subsequent GalT-KO grafts was observed, as well as an increase in the antibody-mediated cytotoxicity to xenogeneic targets (summarized in Table 3 for IgG)).

Similar to the results seen in recipients of primary xenogeneic and subsequent allogeneic grafts, serum IgM and IgG antibodies that specifically bound to allogeneic cells could only be detected by flow cytometry in one of four animals following rejection of primary allografts. However, all recipients demonstrated a significant increase in allogeneic cell lysis following allograft rejection. Taken together, these results suggest that the rejection of secondary GalT-KO xenogeneic skin grafts was due to a specific anti-xenogeneic response, and not due to cross-reactivity of anti-allogeneic antibodies produced as a result of primary allogeneic skin graft rejection.

Discussion

The results reported in this study demonstrate that GalT-KO xenogeneic skin grafts can provide temporary coverage of full thickness defects in baboons comparable to that provided by allogeneic skin. In addition to the similar clinical time course for rejection, the rejection of primary GalT-KO skin grafts leads to an anti-xenogeneic humoral response with no evidence for cross-sensitization to alloantigens, suggesting that GalT-KO skin grafts could provide an early first line treatment in the management of severe burns that would not preclude subsequent use of allografts. It is of note that the robust anti-xenogeneic IgM and IgG antibody responses observed were against non-Gal epitopes, as both the skin grafts as well as target cells used in the various in vitro assays came from GalT-KO animals, deficient in the alpha-1,3 galactosyltransferase gene, and thus not subject to recognition by circulating natural anti-Gal antibodies. Furthermore, we demonstrated that recipients pre-sensitized to alloantigens did not have an increased response or accelerated rejection of GalT-KO xenogeneic skin grafts on subsequent exposure to xenoantigens, indicating that the presence of traditional donor-specific alloantibodies that could be a barrier to the use of allogeneic skin grafts, would not pose such a barrier in the use of GalT-KO skin. The lack of accelerated rejection of secondary grafts, either allogeneic or xenogeneic, was not due to inability to mount a memory response, as previous work in this laboratory has shown that once a recipient has rejected either an allogeneic or xenogeneic graft, subsequent donor-specific grafts were rejected in an accelerated manner.

Although it has been shown previously that xenogeneic antibody responses include production of antibodies to MHC antigens (Sachs et al., J Immunol 1971; 107: 481-492), the more robust response observed against xenogeneic versus allogeneic cell-surface antigens suggests reactivity to additional kinds of antigens in the xenogeneic situation. Nevertheless, the presence of these additional antigens did not lead to an accelerated rejection of the xenogeneic grafts, suggesting that these additional antigens are of less importance for the cellular than for the humoral immune response. Thus, in the absence of Gal antigens, to which the most potent natural antibody reactivities are seen (Weiner et al., Xenotransplantation 2010; 17: 147-152), it would appear that primary skin graft rejection is primarily due to the cellular immune response and is comparable for allogeneic and xenogeneic skin grafts.

From a clinical perspective, the use of GalT-KO xenogeneic skin could avoid many of the disadvantages associated with the use of deceased-donor allogeneic skin, including high cost, limited availability and the risk of human pathogen transmission. The potential risk of transmission of pathogenic organisms as a result of xenotransplantation has been studied extensively and addressed by the FDA (Food and Drug Administration, Center for Biologics Evaluation and Research, Guidance for Industry: Source Animal, Product, Preclinical, and Clinical Issues Concerning the use of Xenotransplantation in Humans. FDA/CBER/DCGT/LCI (HFM-40), 1401 Rockville Pike, Rockville, Md. 20852, USA. Available online at fda.gov/cber/guidelines.htm). While there remains a theoretical concern about potential retroviral transmission, this risk now appears to be very small and, unlike human skin, swine skin can be assured to be free of the more common zoonotic pathogens by the use of animals from a specific pathogen free (SPF) colony (Id.). Again in contrast to deceased-donor skin, swine skin can be produced in essentially unlimited quantities. In addition, swine skin can be cryopreserved and thawed with no significant effect on outcome in comparison to fresh skin (Table 1). The present demonstration that serial grafting of GalT-KO and allogeneic skin is possible in either order, could potentially double the temporary coverage time for severely burned patients, providing an extended period for healing of autologous graft donor sites or the cultivation of suitable autologous skin for long-term coverage. All of these factors could be of significant benefit in the treatment of severe burns.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of transplanting swine cells, tissue, or organ to a human or non-human primate, the method comprising: transplanting a cell, tissue, or organ from a swine to the human or non-human primate, wherein the swine is produced by Cesarean section, wherein the cell, tissue, or organ to be transplanted is free of porcine cytomegalovirus (pCMV), wherein the human or non-human primate is under a chronic immunosuppressive treatment comprising administration of a corticosteroid, wherein the immunosuppressive treatment is in absence of induction therapy, and wherein the cell, tissue, or organ comprises cells of skin, or a renal tissue.

2. The method of claim 1, wherein the swine is a swine that expresses a transgene encoding a human MHC class I protein that inhibits recipient NK cell mediated attack; a swine which is homozygous at swine leukocyte antigens (SLA) A, B, C, DR, and DQ, and in which at least 60% of all other genetic loci are homozygous; or a swine in which the normal expression of alpha(1,3) galactosyltransferase is prevented in at least one organ of tissue type.

3. The method of claim 1, wherein the swine is a miniature swine.

4. The method of claim 1, wherein the cell, tissue, or organ is skin or a skin cell.

5. A method of treating a subject who has suffered an injury requiring a skin graft, the method comprising: transplanting a skin graft from a swine to the subject, wherein the swine is produced by Cesarean section, wherein the skin graft is free of porcine cytomegalovirus (pCMV), wherein the subject is under a chronic immunosuppressive treatment comprising administration of a corticosteroid, wherein the immunosuppressive treatment is in absence of induction therapy.

6. The method of claim 5, further comprising:
monitoring the skin graft for clinical signs of rejection;
after detection of one or more clinical signs of rejection of the skin graft, removing the skin graft and replacing it with an allogeneic skin graft or an autologous skin graft.

7. The method of claim 6, wherein the one or more clinical signs of rejection are selected from the group consisting of lack or loss a vascularization; sloughing; white color; darker or pale color compared to normal skin; cooler temperature as compared to normal skin; granulation; crust or scab formation; discharge; and loss or lessening of pliability.

8. The method of claim 5, wherein the injury is a partial thickness wound or a full thickness wound.

9. The method of claim 8, wherein the injury comprises burns; avulsed skin; diabetic wounds; and/or venous stasis ulcers.

10. The method of claim 5, wherein the subject is a human or non-human primate.

11. The method of claim 5, wherein the skin graft is cryopreserved after harvesting from the swine.

\* \* \* \* \*

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: PCR primer

<400> SEQUENCE: 1
ccctgatctt aaatgacgag gacgtgac                                    28

<210> SEQ ID NO 2
<211> LENGTH: 30
<212> TYPE: DNA
<213> ORGANISM: Artificial Sequence
<220> FEATURE:
<223> OTHER INFORMATION: PCR primer -continued

```
<400> SEQUENCE: 2
accgtctgag agactgaact tctctgacac                                           30
```